United States Patent [19]

Ash et al.

[11] Patent Number: 4,559,039
[45] Date of Patent: Dec. 17, 1985

[54] PERMANENTLY PLACED TRANSCUTANEOUS ACCESS DEVICE TO BLOOD VESSELS

[75] Inventors: Stephen R. Ash; Geraldine M. Kaufman, both of Lafayette, Ind.

[73] Assignee: Purdue Research Foundation, West Lafayette, Ind.

[21] Appl. No.: 557,827

[22] Filed: Dec. 5, 1983

[51] Int. Cl.$^4$ .............................................. A61M 5/00
[52] U.S. Cl. ..................................... 604/175; 604/44; 604/52; 604/272
[58] Field of Search ..................... 604/6, 27, 174, 175, 604/43, 44, 52, 272–274, 905

[56] References Cited

U.S. PATENT DOCUMENTS

| | | | |
|---|---|---|---|
| 1,465,851 | 8/1923 | Kress | 604/273 |
| 2,748,769 | 6/1956 | Huber | 604/272 |
| 3,783,868 | 1/1974 | Bokros | 604/891 |
| 3,870,043 | 3/1975 | Dunn | 604/272 |
| 4,160,454 | 6/1979 | Foux | 604/175 |
| 4,306,545 | 12/1981 | Ivan et al. | 604/175 |
| 4,496,350 | 1/1985 | Cosentino | 604/4 |

FOREIGN PATENT DOCUMENTS 1859825  6/1975  United Kingdom ................ 604/175

OTHER PUBLICATIONS

"A. B. Dick, Operating Instructions" Manuel Models 350CD/360CD/375CD Offset Duplicators, pp. 5–15, 25, 1979.

Primary Examiner—C. Fred Rosenbaum
Assistant Examiner—Karen L. Kaechele
Attorney, Agent, or Firm—Barnes & Thornburg

[57] ABSTRACT

A transcutaneous access device for permanent placement in blood vessels includes a unitarily constructed, substantially U-shaped tubular member that includes a first leg having means for connecting the transcutaneous access device to external equipment, a mid-portion having at least one aperture, and a second leg terminating in a needle barb. The angular orientation of the device is such that the planes that include the first leg and the second leg that are orthogonal to the mid-portion are substantially parallel, and the second leg is at an acute angle with respect to the plane that includes the mid-portion and said first leg.

13 Claims, 6 Drawing Figures

U.S. Patent  Dec. 17, 1985  4,559,039
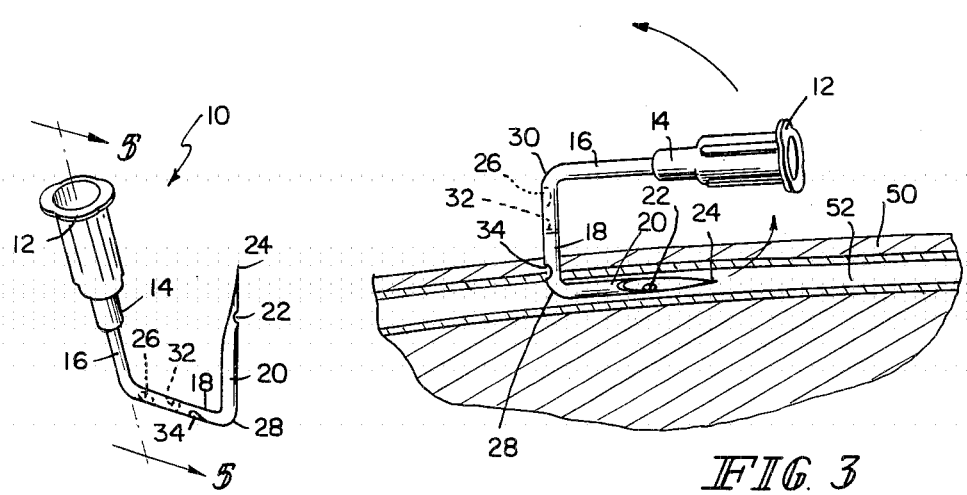
FIG. 1
FIG. 3
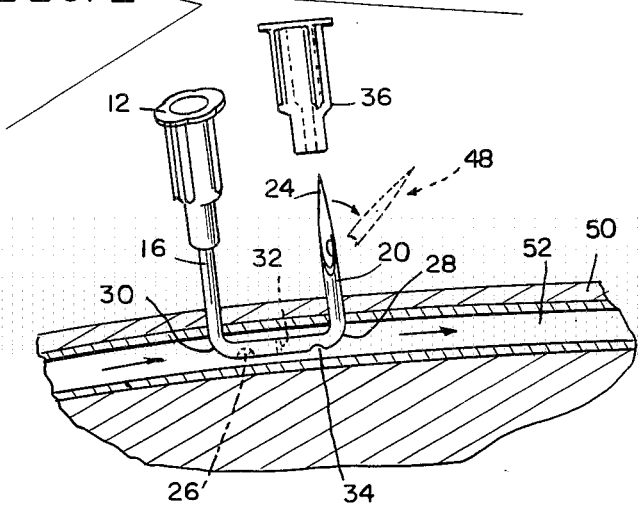
FIG. 4
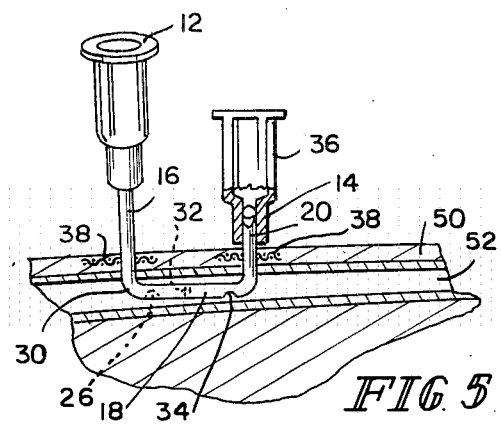
FIG. 5
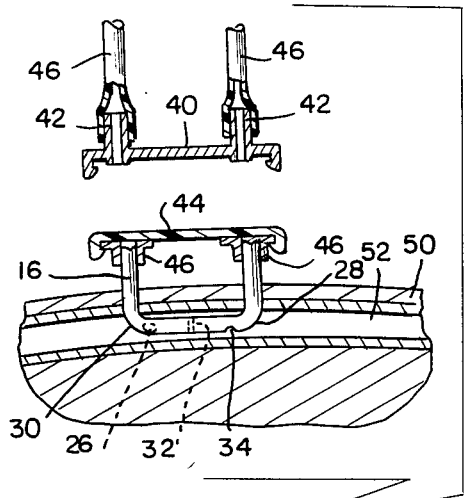
FIG. 6
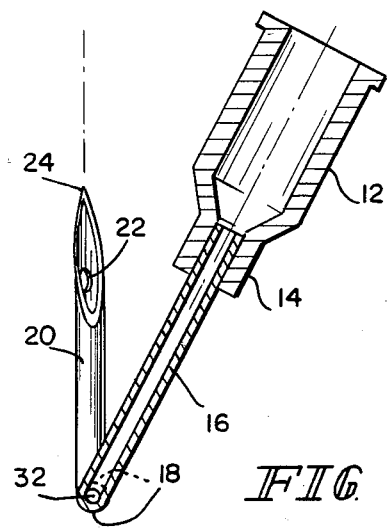
FIG. 2

PERMANENTLY PLACED TRANSCUTANEOUS ACCESS DEVICE TO BLOOD VESSELS

This invention relates to access devices to blood vessels, and more specifically, to a transcutaneous access device suitable for permanent placement by non-surgical implantation.

In a wide variety of medical therapeutic programs it is often necessary to remove blood at a rapid rate from the body. For example, in hemodialysis, a blood flow rate of at least 200 ml/min is required to obtain sufficient chemical clearance in order to decrease the body level of toxins caused by kidney failure. The devices utilized in permitting blood removal from the body are called "blood access devices" and include the arterio-venous shunt (silicone tubes connecting an artery and a vein, penetrating the skin); the arterio-venous fistula (a "window" between an artery and a vein, which results ultimately in a large vein, which may be easily penetrated three times a week); and the "carbon button" device (an artificial, porous vascular graft with a middle segment of carbon, connected to a carbon tube which penetrates the skin).

Each of the aforedescribed access devices has problems associated with its implantation or its subsequent use. With the arterio-venous shunt, one can expect fibrosis and stenosis to occur at the point of connection to the vein. This normally limits the time in which the arterio-venous shunt can be used to approximately four months. The arterio-venous shunt is also extremely expensive to install. Similar problems are encountered in the use of an arterio-venous fistula.

The "carbon button" has a number of drawbacks, including the fact that major surgery is required for implantation, resulting in tremendous costs for the patient. Additionally, there is always a significant risk of infection when a "carbon button" is utilized. Further, a "carbon button" has recirculation between the inflow and outflow tubes within the carbon cylinder.

The novel transcutaneous access device of this invention has numerous advantages over the commercially available access devices. Among those advantages are the following:

(1) The blood access device of the present invention may be placed "medically" in a procedure room or dialysis unit. Because of the size of the device of the present invention, only a local anesthetic need be used in implantation. General anesthesia is not required, and only the skills of a general internist are necessary.

(2) There is minimal foreign body surface contact between the device and the vein or artery.

(3) There is no need for repeated needle sticks for access to a fistula.

(4) The device is quasi-permanent, lasting three to twelve months.

(5) The device is quite inexpensive, resulting in a tremendous saving to a patient.

(6) The device can be used where there is a need for separate inflow and outflow of blood, or where the blood must be taken in and out of a vein in a periodically reversing manner.

Additionally, the device can be used in conjunction with Teflon disks positioned between the blood vessel and skin surface to improve the stability and long-term biocompatibility of the device. Further, the device is compatible with a variety of caps or port covers that provide a sterile seal for the device after use.

It is therefore an object of the present invention to provide a quasi-permanent transcutaneous blood access device that requires only simple medical procedures to be followed for implantation.

Another object is to provide a transcutaneous blood access device that reduces the strain and stress applied to a vein or artery during insertion.

A further object is to provide a transcutaneous blood access device with a configuration that gives improved stability following implantation.

Therefore, a transcutaneous blood access device made in accordance with the present invention includes a unitarily formed, substantially U-shaped hollow member having a first and second leg and a mid-portion. The mid-portion includes at least one access port radially disposed with respect to the central axis of said mid-portion. The second leg includes a connection means for connecting the transcutaneous blood access device to external equipment and the second leg includes a second needle barb to facilitate subsequent breaking of the barb for crimping purposes following implantation of the device.

Further, the angular orientation of a transcutaneous blood access device made in accordance with the present invention is such that the planes that contain the first leg and the second leg that are orthogonal to the mid-portion are substantially parallel to each other. Additionally, the second leg is placed at an acute angle with respect to the plane that includes the first leg and said mid-portion.

Further, a transcutaneous blood access device made in accordance with the present invention includes a mid-portion with two access ports radially offset with respect to each other around the central axis of said mid-portion. Additionally, the device can include a septum or plug centrally disposed in the mid-portion to permit simultaneous inflow into and outflow from said device.

Further, a transcutaneous blood access device made in accordance with the present invention includes a first and a second leg and a mid-portion that are coated with pyrolytic carbon to enhance biocompatability of said device with the tissues of a user.

Further, a transcutaneous blood access device made in accordance with the present invention includes capping devices for selectively sealing the inflow and outflow ports of said device.

Additional features and advantages of the invention will become apparent to those skilled in the art upon consideration of the following detailed description of a preferred embodiment exemplifying the best mode of carrying out the invention as presently perceived. The detailed description particularly refers to the accompanying figures in which:

FIG. 1 is a perspective view of a transcutaneous blood access device made in accordance with the present invention;

FIG. 2 is a partially cut-away sectional view of the transcutaneous blood access device made in accordance with the present invention taken along lines 5—5 as shown in FIG. 1;

FIG. 3 is a cross-sectional view of a vein during implantation of a transcutaneous blood access device made in accordance with the present invention;

FIG. 4 is a cross-sectional view of the vein of FIG. 3 following final placement of the transcutaneous blood access device made in accordance with the present invention;

FIG. 5 is a cross-sectional view of the vein of FIG. 4 following crimping of the barbed portion of the implanted transcutaneous blood access device made in accordance with the present invention; and FIG. 6 is another embodiment of the transcutaneous blood access device following the implantation in a vein made in accordance with the present invention.

A transcutaneous blood access device 10 shown in FIGS. 1-3 includes a hub 12 crimp-sealed to a first leg 16 at crimp-seal point 14, a mid-portion 18, and a second leg portion 20. Legs 16 and 20 and mid-portion 18 define a substantially U-shaped member that is formed from stainless steel tubing having a needle gauge size of from 10 to 20. Mid-portion 18 includes a pair of apertures or access ports 26 and 34 positioned on the periphery of said mid-portion 18. The first access port 26 is toward the first end 30 of said mid-portion 18 proximal to first leg 16. The second access port 34 is towards the second end 28 of the mid-portion 18 that is proximal to the second leg 20. The ports 26 and 34 are radially disposed approximately 30° from each other with respect to the central axis of mid-portion 18 defined by lines 6—6. The first leg 16 is bent at a 90° angle with respect to mid-portion 18. The second leg 20 is bent at a 90° angle with respect to the mid-portion 18 and skewed to first leg 16. The planes containing first leg 16 and second leg 20 that are orthogonal to mid-portion 18 are substantially parallel. The second leg 20 is at an acute angle, from about 0° to about 45°, out of the plane containing the mid-portion 18 and first leg 16. This angular displacement between the two legs 16 and 20 facilitates the implantation process by allowing sufficient clearance upon insertion of barbed portion 24 of leg 20 for the operator to manipulate efficiently and guide the second leg 20 into a vein. The angular displacement between the legs 16 and 20 permits the operator to adequately grasp the transcutaneous access device 10 while maintaining visual contact with the second leg 20 during initial insertion. The operator can thus visually observe the placement of the device 10 and yet have sufficient manipulative capabilities to apply whatever pressure is required to guide the barb 24 of leg 20 through the epidermal region 50 of a patient into the underlying vein 52.

Referring now to FIGS. 3 and 4, the transcutaneous access device 10 is inserted into vein 52 at any convenient access point sufficiently removed from any joint so that when the limb is flexed, the hub 12 of device 10 will not interfere with the ready movement of said limb. The barb 24 of leg 20 is guided along the path of the vein 52 such that leg 20 is coaxially oriented in the vein 52 with respect to the vein wall 54. As aforementioned, this initial penetration and guidance of leg 20 into vein 52 is greatly facilitated by the angular displacement of the two legs 16 and 20, i.e., that leg 20 is at an acute angle out of the plane containing mid-portion 18 and leg 16.

Upon complete insertion of leg 20 into vein 52, the transcutaneous access device 10 is manipulated so that barb 24 repunctures vein 52 at exit point 56 so that as leg 20 is guided back through the epidermis 50 and emerges fully from it, it becomes perpendicular to the surface 58 of said epidermis 50. The mid-portion 18 is thus positioned intravascularly such that it is coaxially oriented with respect to vein wall 54. Upon final positioning of the transcutaneous blood access device 10 within vein 52, the barb 24 can be broken at score point 22 and removed, and hub 36 can be crimped upon the remainder of leg 20 following removal of the barb.

This entire implantation operation requires only the skills of an average internist. The trauma involved in the procedure is minimal, allowing a local anesthetic to be used rather than a general anesthetic, resulting in tremendous savings to a user. The hubs 12 and 36 in cooperation with apertures 26 and 34 define access ports for inflow and/or outflow of blood or any other fluid into or from vein 52. The apertures 26 and 34 can be used in cooperation with each other or, if a septum or plug 32 is placed in the mid-region 60 of mid-portion 18, can be used separately, i.e., blood can be drawn out through aperture 26 and hub 12, treated in, for instance, a hemodialysis unit, and returned back to the vein 52 through hub 36 and aperture 34.

As aforestated, the apertures 26 and 34 are radially displaced with respect to each other and with respect to the central axis of said mid-portion 18. By such displacement, a number of operational problems are minimized or alleviated. During the removal of blood from the vein 52, it is always possible for the vein wall 54 to come into contact with the aperture of the device being utilized for removal of blood, commonly referred to as vein collapse. This problem is even more likely to be encountered in a dual-point access device such as that utilized in the present invention. By radially displacing the apertures 26 and 34 with respect to the central axis of mid-portion 18, the danger of vein collapse is greatly minimized as the suction forces are dispersed over a greater area of the vein wall 52. Additionally, when the device 10 is being used for removing blood from one aperture 26 for treatment and subsequent reinfusing back into the vein 52 through aperture 34, the angular displacement between apertures 26 and 34 reduces the extent to which the reinfused treated blood is drawn back up aperture 26 and retreated.

Referring to FIG. 5, a Teflon disk 38 can be implanted in the epidermal region 50 at the point of penetration and the point of exit of the implanted device 10 to facilitate anchoring the transcutaneous blood access device 10 following such an implantation operation. The Teflon disks 38 help stabilize the device by holding it in a fixed position between the vein 52 and the epidermis 50. The disk 38 also improves the long-term biocompatability of the device 10 with a user. The disk 38 can also be used in conjunction with any other form of stablizing collar to minimize the danger of an accidental unseating of the transcutaneous blood access device 10.

Additionally, the flanges 16 and 20 and mid-portion 18 can be given a coating of pyrolytic carbon which also aids in improving the long-term biocompatability of the device 10 with the user. Biocompatabilty is also enhanced by the minimal foreign body surface contact the device 10 has with a user.

The device 10, by providing various hubs 12 (an alternate such hook-up device is shown in FIG. 6), obviates the need for repeated needle sticks for access to a fistula. A user can "hook-up" to an artificial organ or treatment device by use of any standard connection fittings. The hubs 12 and 36 can be tailored for use with any such connectors that may be required.

The transcutaneous blood access device 10 provides the most economical and effective means for providing repeated access to a blood vessel or artery over a long period of time.

What is claimed is:

1. A transcutaneous access device for permanent placement in blood vessels which comprises a unitarily constructed, substantially U-shaped tubular member that includes a first leg having means for connecting the transcutaneous access device to external equipment, a linear mid-portion having at least one aperture positioned on the periphery thereof, and a second leg terminating in a needle barb, said first and second legs being positioned relative to the mid-portion and to each other so that the first and second legs are generally perpendicular to the mid-portion and the second leg forms an acute angle with a plane that includes the mid-portion and the first leg.

2. The device of claim 1 wherein the acute angle formed by the second leg and the plane that includes the mid-portion and the first leg is about 0° to about 45°.

3. The device of claim 1 wherein the mid-portion includes two apertures penetrating the periphery thereof, a first aperture being positioned toward the first leg, and a second aperture being positioned toward the second leg, said apertures being radially displaced with respect to each other around the central axis of said mid-portion.

4. A transcutaneous access device for permanent placement in blood vessels which comprises a unitarily constructed, substantially U-shaped tubular member that includes a first leg having means for connecting the device to external equipment, a second leg terminating in a needle barb, and a mid-portion including two apertures penetrating the periphery thereof, a first aperture being positioned toward the first leg and a second aperture being positioned toward the second leg, said apertures being radially displaced with respect to each other around the central axis of said mid-portion and wherein the mid-portion also includes a septum disposed between said apertures to permit simultaneous inflow into and outflow from said device.

5. The device of claim 4 wherein the substantially U-shaped tubular member is coated with pyrolytic carbon to facilitate bicompatibility of said device with a user.

6. The device of claim 6 wherein the substantially U-shaped tubular member is a stainless steel tube with a needle gauge size of about 10 to about 20.

7. The device of claim 4 wherein the connection means further comprises a needle hub connectable with a suitably configured shank.

8. The device of claim 4 wherein the needle barb is scored to permit breaking and removal thereof, and thereby to facilitate a crimping operation for securing connection means to the second leg following implantation of said device.

9. The device of claim 8 which includes sterile capping means for said connection means of the first and second legs for installation following implantation of said device.

10. Method for establishing transcutaneous access to a blood vessel using a transcutaneous access device comprising a unitarily constructed, substantially U-shaped tubular member that includes a first leg having means for connecting the transcutaneous access device to external equipment, a mid-portion having at least one aperture and a second leg terminating in a needle barb, said method comprising inserting the second leg of the device transcutaneously into the blood vessel at an entry point, guiding the second leg in and along the path of the blood vessel, manipulating the access device to cause the second leg to repuncture the blood vessel at an exit point and positioning the device so that the mid-portion of the device is located intravascularly between the entry point and the exit point.

11. The method of claim 10 wherein the second leg of the access device is at an acute angle with respect to a plane that includes the mid-portion and the first leg, and wherein the first and second legs are generally perpendicular to the mid-portion.

12. The method of claim 10 wherein the mid-portion of the device includes two apertures penetrating the periphery thereof, a first aperture being positioned toward the first leg, and a second aperture being positioned toward the second leg, said apertures being radially displaced with respect to one another around the central axis of said mid-portion.

13. The method of claim 12 wherein the mid-portion of the device also includes a septum disposed between said apertures to permit simultaneous inflow into and outflow from said device.

* * * * *

UNITED STATES PATENT AND TRADEMARK OFFICE
CERTIFICATE OF CORRECTION

PATENT NO. : 4,559,039

DATED : December 17, 1985

INVENTOR(S) : Stephen R. Ash and Geraldine M. Kaufman

It is certified that error appears in the above-identified patent and that said Letters Patent is hereby corrected as shown below:

At column 5, line 44, delete "6" and insert therefor --5--.

Signed and Sealed this

Eleventh Day of March 1986

[SEAL]

Attest:

DONALD J. QUIGG

Attesting Officer

Commissioner of Patents and Trademarks